United States Patent
Yashima et al.

(10) Patent No.: US 9,603,514 B2
(45) Date of Patent: Mar. 28, 2017

(54) LIQUID SUPPLYING APPARATUS AND ENDOSCOPE REPROCESSING APPARATUS

(71) Applicant: OLYMPUS CORPORATION, Tokyo (JP)

(72) Inventors: Taiki Yashima, Machida (JP); Takaaki Komiya, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/171,180

(22) Filed: Jun. 2, 2016

(65) Prior Publication Data

US 2016/0270646 A1 Sep. 22, 2016

Related U.S. Application Data

(63) Continuation of application No. PCT/JP2015/058327, filed on Mar. 19, 2015.

(30) Foreign Application Priority Data

Jul. 16, 2014 (JP) .................................. 2014-146203

(51) Int. Cl.
*A61B 1/12* (2006.01)
*A61L 2/18* (2006.01)
(Continued)

(52) U.S. Cl.
CPC ................ *A61B 1/123* (2013.01); *A61B 1/12* (2013.01); *A61L 2/18* (2013.01); *B08B 3/04* (2013.01);
(Continued)

(58) Field of Classification Search
None
See application file for complete search history.

(56) References Cited

FOREIGN PATENT DOCUMENTS

JP S59-141930 A 8/1984
JP H10-309254 A 11/1998
(Continued)

OTHER PUBLICATIONS

English Machine translation of WO2013/031388A1.*
(Continued)

*Primary Examiner* — Michael Barr
*Assistant Examiner* — Jason Riggleman
(74) *Attorney, Agent, or Firm* — Scully Scott, Murphy & Presser, PC

(57) ABSTRACT

A liquid supply apparatus includes: a storing tank configured to store a liquid; a supply conduit through which the liquid remained inside the supply conduit flows reversely into the storing tank by a predetermined amount over time, the supply conduit having a first end portion connected to the storing tank; a liquid feeding section which is arranged at the storing tank or the supply conduit, and which is configured to feed the liquid from the storing tank to a second end portion of the supply conduit; a time measuring section which measures an elapsed time from stop of the liquid feeding by the liquid feeding section; and a control section which is connected to the liquid feeding section and the time measuring section and which is configured to drive the liquid feeding section for a predetermined time based on a length of the elapsed time.

7 Claims, 11 Drawing Sheets

(51) Int. Cl.
  *B08B 3/08* (2006.01)
  *B67D 7/62* (2010.01)
  *B67D 7/76* (2010.01)
  *G05D 7/06* (2006.01)
  *B08B 3/04* (2006.01)
  *B01J 4/00* (2006.01)

(52) U.S. Cl.
  CPC .............. *B08B 3/08* (2013.01); *B67D 7/62* (2013.01); *B67D 7/763* (2013.01); *G05D 7/0676* (2013.01); *A61L 2202/24* (2013.01); *B01J 4/00* (2013.01)

(56) References Cited

FOREIGN PATENT DOCUMENTS

JP  2010-057752 A  3/2010
WO  WO2013/031388 A1 * 3/2013

OTHER PUBLICATIONS

International Search Report dated Jun. 16, 2015 issued in PCT/JP2015/058327.
Japanese Office Action dated Nov. 14, 2015 issued in JP 2015-537863.

\* cited by examiner

LIQUID SUPPLYING APPARATUS AND ENDOSCOPE REPROCESSING APPARATUS

CROSS REFERENCE TO RELATED APPLICATION

This application is a continuation application of PCT/JP2015/058327 filed on Mar. 19, 2015 and claims benefit of Japanese Application No. 2014-146203 filed in Japan on Jul. 16, 2014, the entire contents of which are incorporated herein by this reference.

BACKGROUND OF THE INVENTION

1. Field of the Invention

The present invention relates to a liquid supply apparatus and an endoscope reprocessing apparatus that include a liquid supply conduit for discharging a liquid in a storing tank.

2. Description of the Related Art

Endoscopes for use in medical fields are subjected to processing using fluid such as cleaning processing and disinfecting processing after being used. As an apparatus that automatically performs cleaning processing and disinfecting processing on an endoscope, for example, the endoscope reprocessing apparatus as disclosed in Japanese Patent Application Laid-Open Publication No. 2010-57752 is known.

The endoscope reprocessing apparatus is provided with a liquid supply apparatus that stores a liquid such as cleaning solution, disinfectant solution, or the like and discharges a predetermined amount of liquid according to the progress of processing processes. As disclosed in Japanese Patent Application Laid-Open Publication No. 2010-57752, the liquid supply apparatus includes a storing tank that stores a liquid, a supply conduit including a first end portion that opens in the storing tank and a second end portion that opens at a position upper than the storing tank, and a liquid feeding section such as a pump provided to the supply conduit.

In the liquid supply apparatus having such a configuration, when the liquid feeding section is in a stopped state, the liquid in the supply conduit returns to the storing tank, which allows entering of air into the supply conduit. Presence of air in the supply conduit causes unevenness in the volume of the liquid discharged from the liquid supply apparatus. In view of the above, the conventional liquid supply apparatus causes the liquid feeding section to be operated for a predetermined time, prior to discharge of a liquid, and performs an air venting process for releasing air entered into the supply conduit.

SUMMARY OF THE INVENTION

A liquid supply apparatus according to one aspect of the present invention includes: a storing tank configured to store a liquid; a supply conduit through which the liquid remained inside the supply conduit flows reversely into the storing tank by a predetermined amount over time, the supply conduit having a first end portion connected to the storing tank; a liquid feeding section which is arranged at the storing tank or the supply conduit, and which is configured to feed the liquid from the storing tank to a second end portion of the supply conduit; a time measuring section which measures an elapsed time from stop of the liquid feeding by the liquid feeding section; and a control section which is connected to the liquid feeding section and the time measuring section and which is configured to drive the liquid feeding section for a predetermined time based on a length of the elapsed time.

An endoscope reprocessing apparatus according to one aspect of the present invention includes: the liquid supply apparatus and a processing basin in which an endoscope can be arranged and into which the liquid supplied from the liquid supply apparatus is introduced.

DETAILED DESCRIPTION OF THE PREFERRED EMBODIMENT(S)

Figure 1:
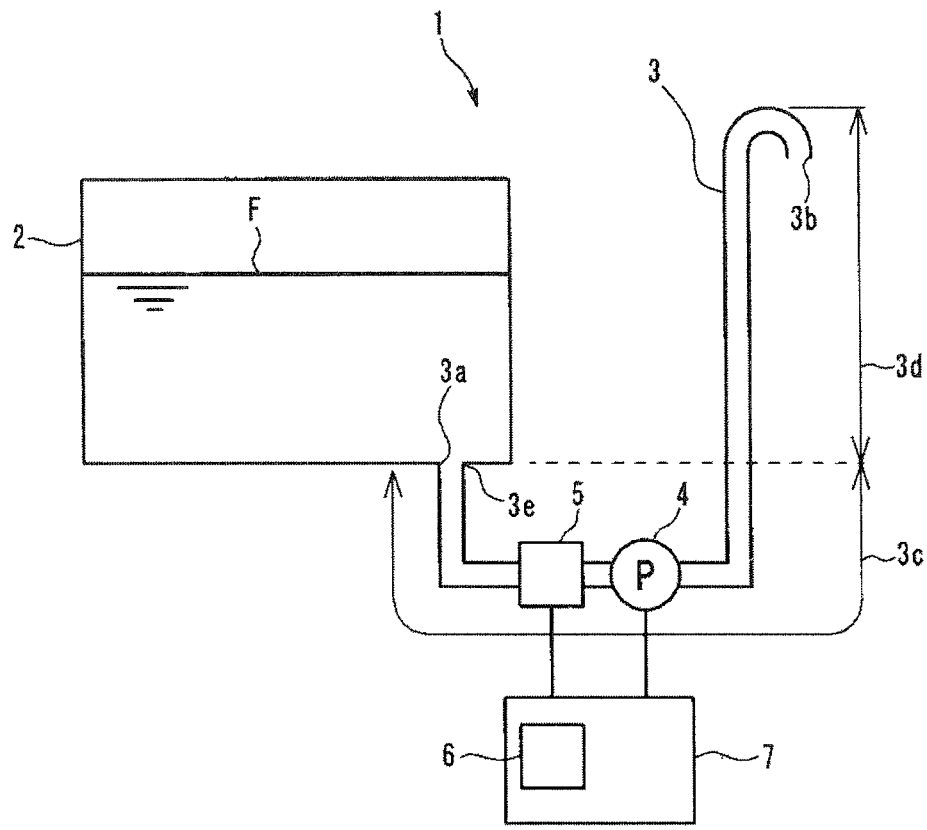
FIG. 1 illustrates a configuration of a liquid supply apparatus according to a first embodiment.

Hereinafter, embodiments of the present invention will be described with reference to drawings. Note that, in the drawings to be used for the description below, a different scale size is used for each of the constituent elements in order to allow each of the constituent elements to be illustrated in a recognizable size on the drawings, and the present invention is not limited only to the number, shapes, ratio of the sizes of the constituent elements, and a relative positional relationship among the constituent elements shown in these drawings.

First Embodiment

Hereinafter, description will be made on the first embodiment as one example of the embodiments of the present invention. A liquid supply apparatus 1 according to the present embodiment as shown in FIG. 1 includes a storing tank 2 that stores a liquid F, a supply conduit 3 including a first end portion 3a connected to the storing tank 2, and a liquid feeding section 4 that feeds the liquid F in the storing tank 2 to a second end portion 3b of the supply conduit 3 through the supply conduit 3. In addition, the liquid supply apparatus 1 includes a liquid flow detection section 5, a time measuring section 6, and a control section 7.

Schematically, the liquid supply apparatus 1 is an apparatus that operates the liquid feeding section 4, to thereby discharge the liquid F in the storing tank 2 from the second end portion 3b of the supply conduit 3. The liquid supply apparatus 1 is incorporated in an apparatus that uses the liquid F. As described later, in the present embodiment, the liquid supply apparatus 1 is incorporated in an endoscope reprocessing apparatus 20 that uses the liquid F as one example shown in FIG. 2.

Hereinafter, in order to describe the positional relationship among the constituent elements, upper and lower directions will be referred to. These directions indicate the upper side in the direction of gravitational force and the lower side in the gravitational force, respectively, in the state where the liquid supply apparatus 1 and the endoscope reprocessing apparatus 2 are arranged in a usable posture. The upper side in the direction of gravitational force is a direction of getting away from a gravitational source, and the lower side in the direction of gravitational force is a direction of getting close to the gravitational source.

The liquid supply apparatus 1 is provided with an electric power supply section for supplying electric power to the respective sections that require electric power, though not shown. The electric power supply section may be configured to get electric power from outside, for example, a commercial power source, or may be configured to include a power generating device or a battery to get electric power therefrom.

The control section 7 includes an arithmetic device (CPU), a memory device (RAM), an auxiliary memory device, an input/output device, an electric power control apparatus, etc., and configured such that motions of the respective sections that configure the liquid supply apparatus 1 are controlled based on a predetermined program.

The control section 7 includes the time measuring section 6 that recognizes the elapsed time from a predetermined clock time. The time measuring section 6 may be a timer that counts the elapsed time from the predetermined clock time, or may be configured to recognize the elapsed time from the predetermined clock time by comparing the stored predetermined clock time (date and time) and a current clock time. Note that the time measuring section 6 may be configured independently from the control section 7.

Note that, when the liquid supply apparatus 1 is incorporated in the apparatus (endoscope reprocessing apparatus 20 in the present embodiment) that uses the liquid F, a part of or an entirety of the configurations of the control section 7 and the electric power supply section may be shared with the apparatus that uses the liquid F. That is, the control section 7 may have a configuration for controlling not only the motions of the sections in the liquid supply apparatus 1 but also the motions of the respective sections that constitute the endoscope reprocessing apparatus 20 based on a predetermined program. In addition, the electric power supply section may have a configuration for supplying electric power not only to the sections in the liquid supply apparatus 1 but also to the respective sections that constitute the endoscope reprocessing apparatus 20.

The storing tank 2 is a part in which the liquid F is stored. The storing tank 2 has a container shape, the upper part of which is closed in the present embodiment shown in the drawings. However, the storing tank 2 has only to be a member having therein a space for retaining the liquid F. For example, the storing tank 2 may have a tub shape configured such that the upper part is open to the atmosphere. Note that the storing tank 2 may be configured to be detachable. In addition, the storing tank 2 is not limited to a configuration made of a member having a predetermined rigidity, but may have a bag-like shape made of a flexible member.

The supply conduit 3 is a conduit which includes a first end portion 3a connected to the storing tank 2 and which is extended outside the storing tank 2. The first end portion 3a of the supply conduit 3 opens in the storing tank 2, and a second end portion 3b opens at an outside of the storing tank 2. The second end portion 3b of the supply conduit 3 is connected to a processing basin 22 included in the endoscope reprocessing apparatus 20 to be described later.

In the present embodiment, the first end portion 3a of the supply conduit 3 opens on the bottom face of the storing tank 2, as one example. Note that the first end portion 3a of the supply conduit 3 is not limited to the configuration opening on the bottom face of the storing tank 2 as shown in the drawings, but may be disposed at a position apart upward from the lowest position of the bottom face by a predetermined distance. Further, the first end portion 3a of the supply conduit 3 may open on the side face of the storing tank 2. Furthermore, the first end portion 3a of the supply conduit 3 may open at plural positions in the storing tank 2.

The other end (second end portion) 3b of the supply conduit 3 is disposed at a position upper than the maximum liquid level height of the storing tank 2. The maximum liquid level height is the maximum height that the liquid level of the liquid F can reach in the storing tank 2, and is the full water level of the storing tank 2 or the water level at which the water level sensor provided in the storing tank is arranged, for example. The second end portion 3b of the supply conduit 3 is located at the position upper than the maximum liquid level height, which prevents the liquid F in the storing tank 2 from flowing out from the second end portion 3b through the conduit 3 based on the principle of siphon during the stop of the liquid feeding section 4. Note that the second end portion 3b of the supply conduit 3 opens downward in the present embodiment shown in the drawings. However, the opening direction of the second end portion 3b is not limited in particular.

In addition, since the second end portion 3b of the supply conduit 3 is located at the position upper than the maximum liquid level height of the storing tank 2, the liquid F remained inside the supply conduit 3 returns to the storing tank 2 by a predetermined amount over time during the stop of the liquid feeding section 4. The direction of the flow of the liquid F in the supply conduit 3 during the stop of the liquid feeding section 4 is opposite to the direction in which the liquid F flows in the supply conduit 3 by operating the liquid feeding section 4, and can be referred to as a reverse flow.

More specifically, the supply conduit 3 according to the present embodiment is constituted of two sections, i.e., a first conduit 3c located on the first end portion 3a side and a second conduit 3d located on the second end portion 3b side. The first conduit 3c is the section including a first connection portion 3e connected to the storing tank 2 and located at a position lower than the storing tank 2. The second conduit 3d is the section between the first conduit 3c and the second end portion 3b, which is arranged at the position upper than the first connection portion 3e.

The supply conduit 3 is provided with the liquid feeding section 4 and a liquid flow detection section 5, which will be described later. The supply conduit 3 may be branched off at a position closer to the second end portion 3b side with respect to the liquid feeding section 4. That is, the supply conduit 3 may include a plurality of second end portions 3b.

The liquid feeding section 4 is a pump that transfers the fluid in the supply conduit 3 from the first end portion 3a toward the second end portion 3b. The liquid feeding section 4 is disposed at the first conduit 3c in the present embodiment. Operation of the liquid feeding section 4 causes the liquid F in the storing tank 2 to be transferred through the supply conduit 3 from the first end portion 3a toward the second end portion 3b, and then to be discharged from the second end portion 3b. The liquid feeding section 4 is electrically connected to the control section 7 and the motion of the liquid feeding section 4 is controlled by the control section 7.

The liquid feeding section 4 does not have a configuration, such as a check valve, for completely stopping the flow, which is from the second end portion 3b to the first end portion 3a, of the fluid in the supply conduit 3. That is, while the liquid feeding section 4 is stopped, the liquid feeding section 4 serves as a constriction section that constricts the cross-sectional area of the supply conduit 3 and causes a resistance to the flow of the fluid in the supply conduit 3. However, the liquid feeding section 4 does not block the flow. Such a pump is common. The liquid feeding section 4 is configured not to block the reverse flow during the stop thereof, which can simplify the configuration of the liquid feeding section. Note that the liquid feeding section 4 may be provided with a loose check valve that does not completely block the flow, which is from the second end portion 3b to the first end portion 3a, of the fluid in the supply conduit 3.

In the present embodiment, the first conduit 3c is located at the position lower than the storing tank 2. Therefore, the liquid F is always present in the first conduit 3c. That is, the liquid F is always present in the liquid feeding section 4, and the variation of the liquid level height in the conduit 3 in the case where the liquid F in the conduit 3 flows reversely by the stop of the liquid feeding section occurs only in the section of the second conduit 3d.

The liquid feeding section 4 serves as the constriction section that causes resistance to the flow of the liquid F during the stop, as described above. Therefore, the flow rate of the liquid F in the case where the liquid F remained in the supply conduit 3 flows reversely into the storing tank 2 during the stop of the liquid feeding section 4 is always defined based on the flow resistance generated by the presence of the liquid feeding section 4. The flow rate is a volume of the liquid F passing through the liquid feeding section 4 per unit time.

Therefore, when the liquid level of the liquid F remained in the supply conduit 3 is located at the position upper than the liquid level in the storing tank 2 and the liquid feeding section 4 is stopped, the liquid F in the supply conduit 3 flows reversely into the storing tank 2 and the liquid level in the supply conduit 3 falls with the elapse of time. If the liquid level in the supply conduit 3 falls, air enters from the second end portion 3b into the supply conduit 3. The flow rate of the liquid F flowing reversely in the supply conduit 3 is limited by the liquid feeding section 4 as the constriction section, which allows the liquid level in the supply conduit 3 to fall at a relatively slow speed. If the elapsed time after the stop of the liquid feeding section 4 is long enough, the liquid level in the supply conduit 3 becomes equal to the liquid level in the storing tank 2.

The liquid flow detection section 5 detects the flow of the liquid at the part where the liquid flow detection section 5 is disposed in the supply conduit 3. The liquid flow detection section 5 is electrically connected to the control section 7.

The liquid flow detection section 5 is disposed at the first conduit 3c in the present embodiment.

The configuration of the liquid flow detection section 5 is not limited in particular, as long as the liquid flow detection section detects the flow of the liquid. As one example in the present embodiment, the liquid flow detection section 5 is configured as a flowmeter. Since the liquid flow detection section 5 is configured as the flowmeter, the liquid supply apparatus 1 is capable of controlling the volume of the liquid F to be discharged.

Note that the method of measuring the flow rate in the supply conduit 3 with the liquid flow detection section 5 is not limited in particular. As one example in the present embodiment, the liquid flow detection section 5 is what is called a turbine flowmeter having a turbine that rotates in accordance with the flow of the liquid F in the liquid supply conduit 3.

Note that the liquid flow detection section 5 is disposed on the first end portion 3a side with respect to the liquid feeding section 4 in the liquid supply conduit 3 in the present embodiment shown in the drawings. However, the liquid flow detection section 5 may be disposed on the second end portion 3b side with respect to the liquid feeding section 4.

Next, the schematic configuration of the endoscope reprocessing apparatus 20 including the liquid supply apparatus 1 will be described. The endoscope reprocessing apparatus 20 is an apparatus that performs rinsing processing, cleaning processing, and disinfecting processing by using water, cleaning solution and disinfectant solution on at least one of the endoscope and endoscope accessories (both are not shown).

Figure 2:
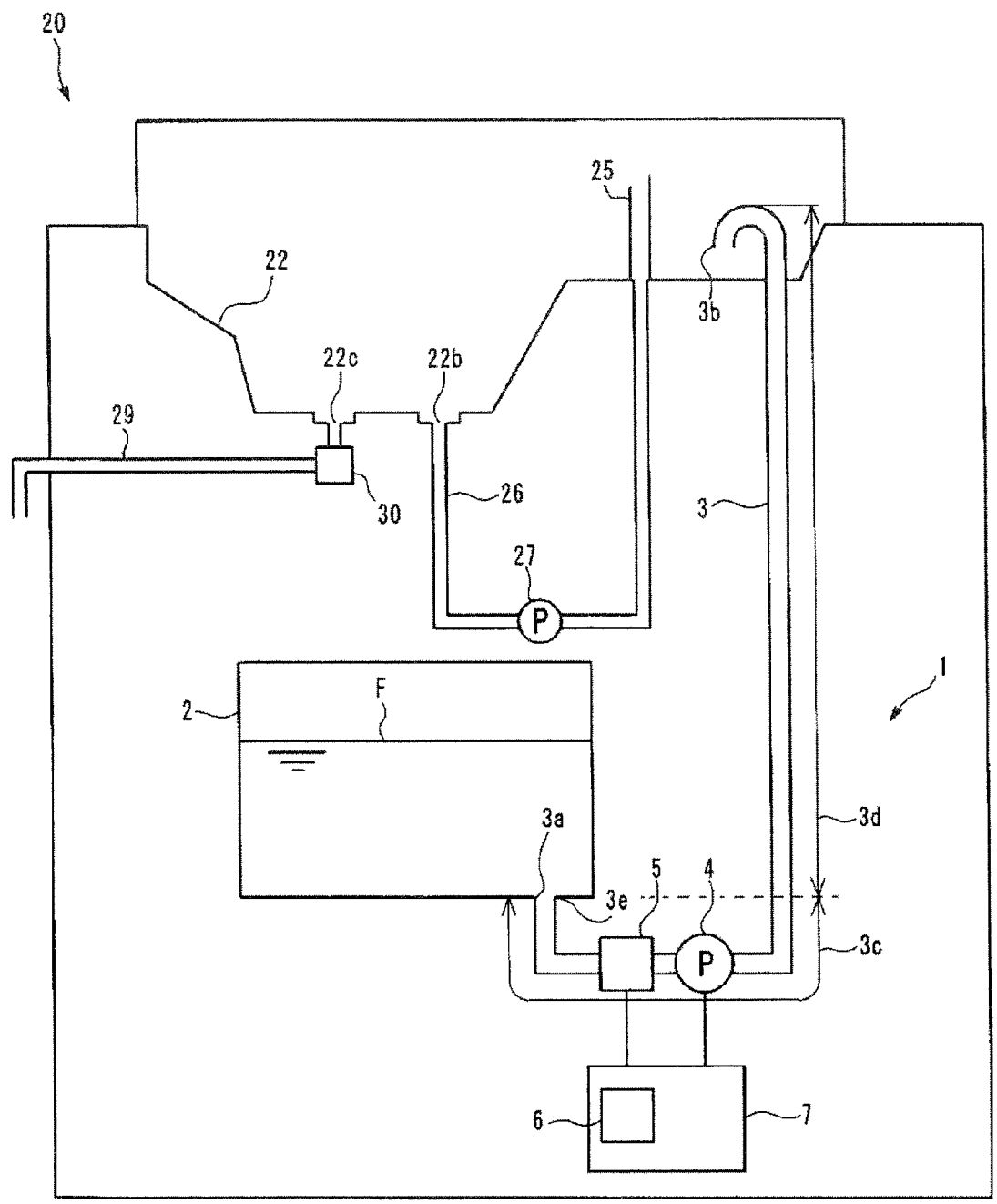
FIG. 2 illustrates a configuration of an endoscope reprocessing apparatus provided with the liquid supply apparatus according to the first embodiment.

As shown in FIG. 2, the endoscope reprocessing apparatus 20 includes a processing basin 22 for disposing at least one of the endoscope and endoscope accessories, and the liquid supply apparatus 1. As one example in the present embodiment, the motion of the endoscope reprocessing apparatus 20 is controlled with the same configuration as that of the control section 7 in the liquid supply apparatus 1. Note that the endoscope reprocessing apparatus 20 may include a control section different from the control section 7 in the liquid supply apparatus 1.

The processing basin 22 has a recessed shape having an opening portion that opens upward, and is configured to be able to house therein at least one of the endoscope and endoscope accessories. The processing basin 22 is configured to be able to store liquid inside.

The storing tank 2 of the liquid supply apparatus 1 is disposed at a position lower than the processing basin 22. In addition, the second end portion 3b of the supply conduit 3 in the liquid supply apparatus 1 is disposed at such a position that the liquid F discharged from the other end is poured in the processing basin 22. That is, the second end portion 3b of the supply conduit 3 opens at the position upper than the processing basin 22. As one example, the liquid supply apparatus 1 retains the liquid F as the cleaning solution in the storing tank 2, and pours a predetermined amount of the liquid F into the processing basin 22 at the time of cleaning processing. Note that the endoscope reprocessing apparatus 20 may be provided with a plurality of liquid supply apparatuses 1 that use different types of liquid.

In addition, a circulation nozzle 25 is disposed in the processing basin 22. The processing basin 22 includes at a lower portion thereof a circulation port 22b and a liquid drainage port 22c. The circulation nozzle 25 communicates with the circulation port 22b through a circulation conduit 26.

The circulation conduit 26 is provided with a circulation pump 27. Operation of the circulation pump 27 allows the liquid in the processing basin 22 to be sucked out from the circulation port 22b and then to be returned to the processing basin 22 via the circulation conduit 26 and the circulation nozzle 25. The endoscope reprocessing apparatus 20 houses at least one of the endoscope and endoscope accessories in the processing basin 22, to perform rinsing processing, disinfecting processing, and the like on at least one of the endoscope and endoscope accessories by circulating water, cleaning solution, and the like.

The liquid drainage port 22c communicates with a drainage conduit 29. The drainage conduit 29 is provided with a valve 30. When the valve 30 is brought into an open state, the liquid retained in the processing basin 22 is ejected outside the processing basin 22 through the drainage conduit 29 by the gravitational force.

Note that the endoscope reprocessing apparatus 20 includes, in addition to the above-described configuration, a configuration for retaining the disinfectant solution and pouring the disinfectant solution into the processing basin 22, a configuration for sending water and air into the processing basin 22, and the like. However, since these configurations are the same as those in known endoscope reprocessing apparatuses, descriptions thereof will be omitted.

Next, description will be made on the motions of the liquid supply apparatus 1 and the endoscope reprocessing apparatus 20 that are configured as described above, with reference to the flowcharts in FIGS. 3 and 4.

Figure 3:
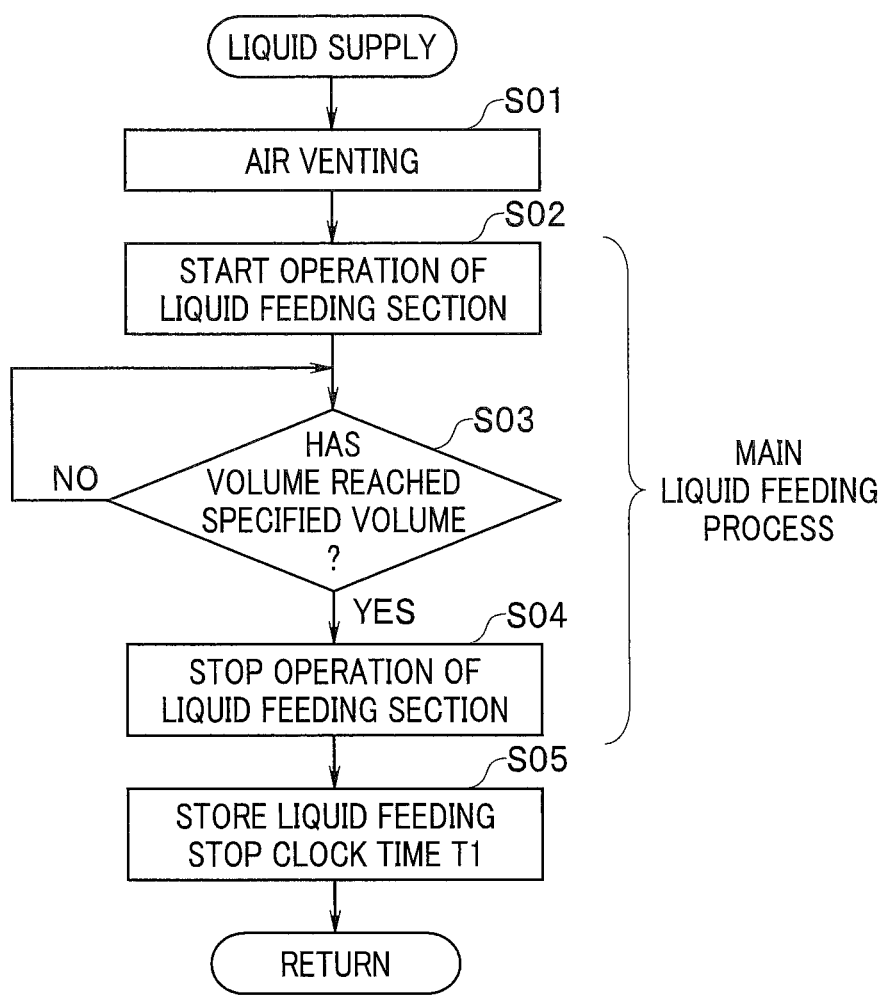
FIG. 3 is a flowchart of a liquid feeding processing according to the first embodiment.

FIG. 3 illustrates a liquid feeding processing routine in which the liquid supply apparatus 1 pours a predetermined volume of the liquid F into the processing basin 22 when the endoscope reprocessing apparatus 20 is actuated. The liquid F is the cleaning solution as one example in the present embodiment. The liquid feeding processing shown in FIG. 3 is performed during the execution of the cleaning processing by the endoscope reprocessing apparatus 20. The respective processes described below are executed based on the control by the control section 7.

In the liquid feeding processing, an air venting process is performed first as shown in step S01. The air venting process is executed based on the flowchart shown in FIG. 4, and the detailed description will be made later. Schematically, the air venting process is such a process that the liquid feeding section 4 is operated until the liquid F is discharged from the second end portion 3b of the supply conduit 3, to fill the entirety of the inside of the supply conduit 3 with the liquid F, and air is released from the inside of the supply conduit 3. After the air venting process in the step S01 is terminated, the processing proceeds to step S02.

In the main liquid feeding process as shown in steps 02 to 04, the liquid feeding section 4 is operated until a specified volume of the liquid F is discharged from the second end portion 3b of the supply conduit 3. In the present embodiment, the specified volume may have a previously set fixed value or a value calculated by the control section 7 based on a predetermined program.

The volume of the liquid F discharged from the second end portion 3b of the supply conduit 3 is calculated by integrating the detection result obtained by the liquid flow detection section 5 as the flowmeter in the present embodiment. Note that the volume of the liquid F discharged from the second end portion 3b of the supply conduit 3 may be estimated from the operation continuing time of the liquid feeding section 4.

Prior to the main liquid feeding process, the air venting process in the step S01 has been performed. Therefore, at the start of the main liquid feeding process, the entirety of the inside of the supply conduit 3 is filled with the liquid F and air is not present in the supply conduit 3. Accordingly, air bubbles are not contained in the liquid F discharged from the second end portion 3b of the supply conduit 3 in the main liquid feeding process, and the specified volume of the liquid F can be accurately discharged from the second end portion 3b of the supply conduit 3 in the main liquid feeding process. After the main liquid feeding process in the steps 02 to 04 has been terminated, the processing proceeds to step S05.

In the step S05, the clock time T1 at which the liquid feeding in the main liquid feeding process executed just before the step S05 was stopped is stored in the time measuring section 6. Note that the clock time T1 may be the clock time at which the control section 7 outputs an instruction for stopping the operation of the liquid feeding section 4 or may be the clock time at which the liquid flow detection section 5 detects that the flow of the liquid F in the supply conduit 3 is stopped. As one example in the present embodiment, the clock time at which the liquid flow detection section 5 detects that the flow of the liquid F in the supply conduit 3 is stopped is defined as the clock time T1. A slight difference occurs between the clock time at which the control section 7 outputs the instruction for stopping the liquid feeding section 4 and the clock time at which the feeding of the liquid F in the supply conduit 3 is actually stopped. Therefore, the clock time at which the stop of the flow of the liquid F in the supply conduit 3 is detected is defined as the clock time T1 as in the present embodiment, thereby capable of more accurately calculating a preliminary liquid feeding time Tp in step S10 to be described later.

Figure 4:
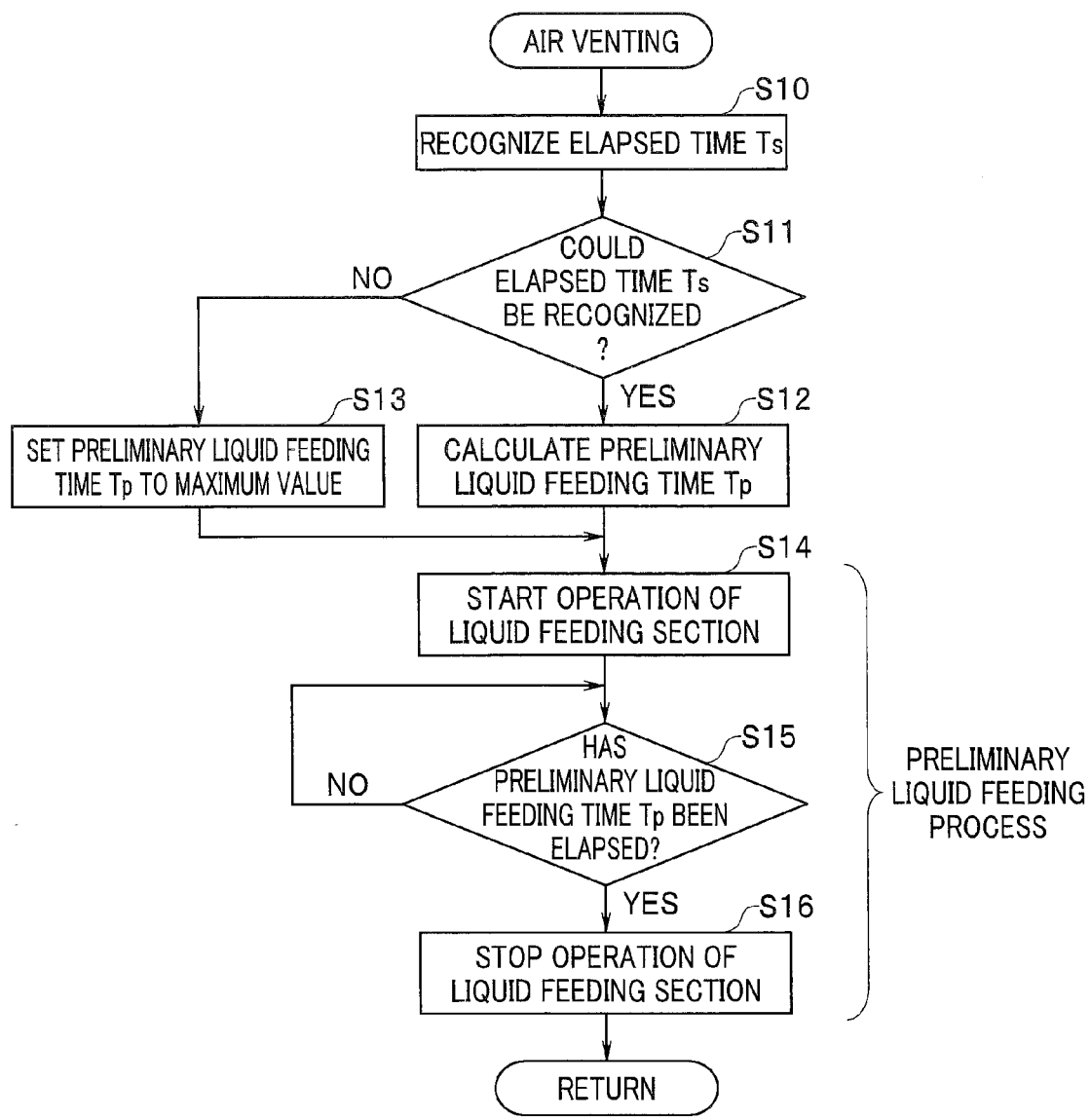
FIG. 4 is a flowchart of an air venting process according to the first embodiment.

Next, detail of the air venting process in step S01 will be described with reference to the flowchart in FIG. 4.

In the air venting process, first in step S10, the time measuring section 6 recognizes an elapsed time Ts from the clock time at which the liquid feeding by the liquid feeding section 4 was stopped last time to the current clock time. Specifically, the time measuring section 6 calculates the elapsed time Ts from the difference between the current clock time and the stored clock time T1 at which detection was made that the flow of the liquid F in the supply conduit 3 was stopped.

In the step S10, when the elapsed time Ts can be recognized (YES in step S11), the processing proceeds to step S12.

Figure 5:
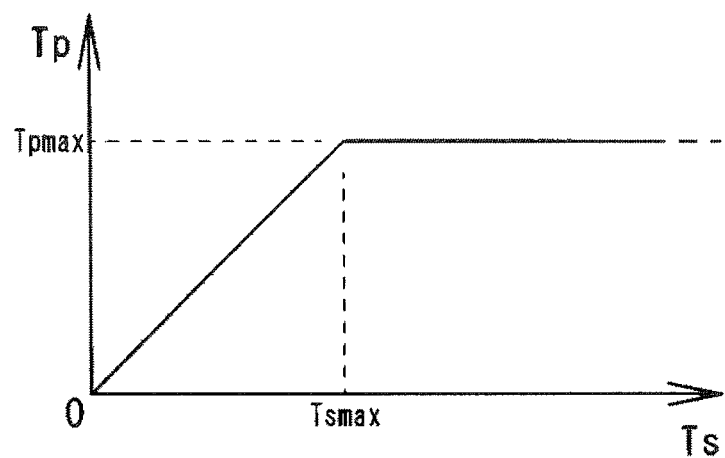
FIG. 5 illustrates a relationship between preliminary liquid feeding time Tp and elapsed time Ts according to the first embodiment.

In step S12, the preliminary liquid feeding time Tp is calculated based on the elapsed time Ts. The longer the elapsed time Ts, the longer the preliminary liquid feeding time Tp becomes. The preliminary liquid feeding time Tp is determined based on the reference table as shown in FIG. 5, for example. Note that the elapsed time Ts and the preliminary liquid feeding time Tp are in a linear relationship in the example shown in FIG. 5. However, the preliminary liquid feeding time Tp may change in a phased manner such that the longer the elapsed time Ts, the longer the preliminary liquid feeding time Tp becomes.

The preliminary liquid feeding time Tp is a value to be used in the preliminary liquid feeding process as shown in steps S14 to S16 to be executed next. The preliminary liquid feeding process in steps S14 to S16 is a process of operating the liquid feeding section 4 only for the preliminary liquid feeding time Tp.

As described above, the present embodiment provides a configuration in which the reverse flow of the liquid F is not blocked during the stop of the liquid feeding section 4. When the liquid feeding section 4 is in the stopped state, the liquid level in the supply conduit 3 falls with the elapse of time, and air enters into the supply conduit 3. Therefore, in the present embodiment, the liquid feeding section 4 is operated only for the preliminary liquid feeding time Tp in the preliminary liquid feeding process, to thereby release the air in the supply conduit 3 and fill the entirety of the inside of the supply conduit 3 with the liquid F. As described above, the air in the supply conduit 3 is released, to thereby enable the specified volume of the liquid F to be accurately discharged in the main liquid feeding process in the steps S02 to S04.

The longer the elapsed time Ts during which the liquid feeding section 4 is in the stopped state, the lower the liquid level in the supply conduit 3. As a result, the amount of the air that enters the supply conduit 3 becomes large. In view of the above, in the present embodiment, the longer the elapsed time Ts, the longer the preliminary liquid feeding time Tp is set, as shown in FIG. 5. The preliminary liquid feeding time Tp is set to such a value that all the air entered into the supply conduit 3 is discharged from inside of the supply conduit 3 by operating the liquid feeding section 4. Since the relationship between the elapsed time Ts and the preliminary liquid feeding time Tp is different depending on the configurations of the supply conduit 3 and the liquid feeding section 4 as the constriction section, the relationship is determined based on an experiment performed in advance, for example.

Note that the elapsed time Ts is longer than a predetermined time Tsmax, the preliminary liquid feeding time Tp is set to a constant maximum value Tpmax irrespective of the length of the elapsed time Ts. The Tsmax in the present embodiment is the time required for the liquid level of the liquid F in the supply conduit 3 to fall to the height at which the liquid level is the lowest. Specifically, the height at which the liquid level of the liquid F in the supply conduit 3 is the lowest in the present embodiment is the height of the lower end of the second conduit 3d, that is, equal to the height of the first connection portion 3e. The value of Tsmax is also different depending on the configurations of the supply conduit 3 and the liquid feeding section 4 as the constriction section. Therefore, the value is determined based on the experiment performed in advance, for example.

In addition, when the elapsed time Ts cannot be recognized in the step S10 (NO in step S11), the processing proceeds to step S13, and the preliminary liquid feeding time Tp is set to the maximum value Tpmax, and thereafter the preliminary liquid feeding process in steps S14 to S16 is executed.

As described above, with the liquid supply apparatus 1 according to the present embodiment, the shorter the elapsed time Ts during which the liquid feeding section 4 is in the stopped state, the shorter the preliminary liquid feeding time Tp during which the liquid feeding section 4 is operated in the air venting process is set.

Therefore, in the present embodiment, the shorter the elapsed time Ts during which the liquid feeding section 4 is in the stopped state, the smaller the amount of the liquid F to be discharged by the execution of the air venting process can be. In addition, the shorter the elapsed time Ts during which the liquid feeding section 4 is in the stopped state, the shorter the preliminary liquid feeding time Tp is set. As a result, the time required for the execution of the air venting process can be shortened. Thus, the liquid supply apparatus 1 and the endoscope reprocessing apparatus 20 in the present embodiment are capable of reducing the consumption amount of the liquid F in the air venting process, and also reducing the time required for the air venting process.

Note that description has been made supposing that the liquid feeding section 4 is stopped during the time after the air venting process in the step S01 and before the subsequent main liquid feeding process in the steps S02 to 04 in the present embodiment. However, the liquid feeding section 4 does not have to be stopped, but may be continued to be operated during the time after the air venting process and before the main liquid feeding process.

Note that the control section 7 changes the preliminary liquid feeding time Tp during which the liquid feeding section 4 is operated in the preliminary liquid feeding process, based on the elapsed time Ts in the present embodiment. However, the control section 7 may change the volume Vp of the liquid F to be fed by the liquid feeding section 4 in the preliminary liquid feeding process, based on the elapsed time Ts.

Figure 6:
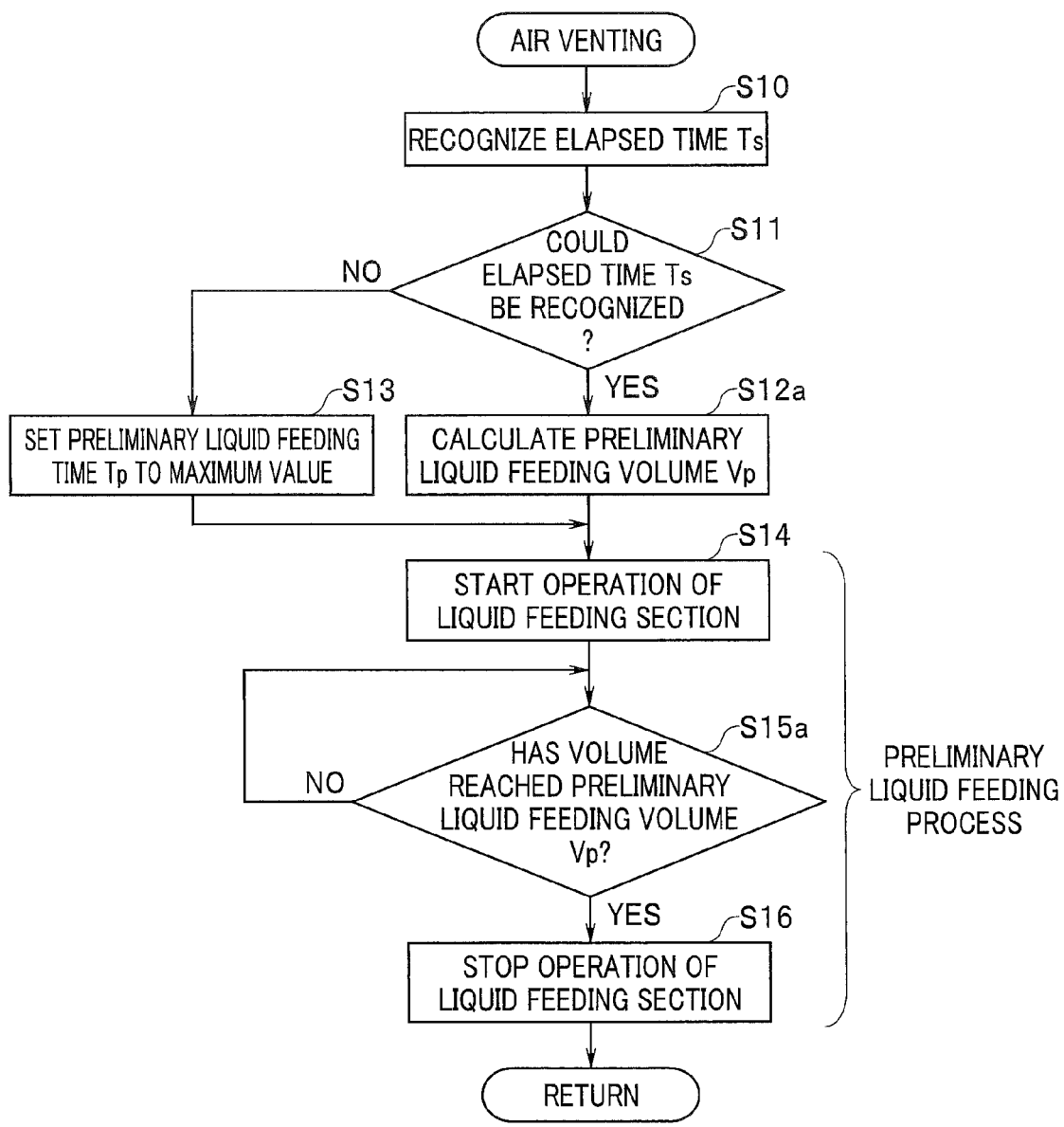
FIG. 6 is a flowchart of a modified example of the air venting process according to the first embodiment.

FIG. 6 illustrates a flowchart of the air venting process in the liquid supply apparatus 1 according to a present modified example. In the present modified example, in step S12a, a preliminary liquid feeding volume Vp as a target value of the volume of the liquid F to be fed by the liquid feeding section 4 in the preliminary liquid feeding process is calculated.

Figure 7:
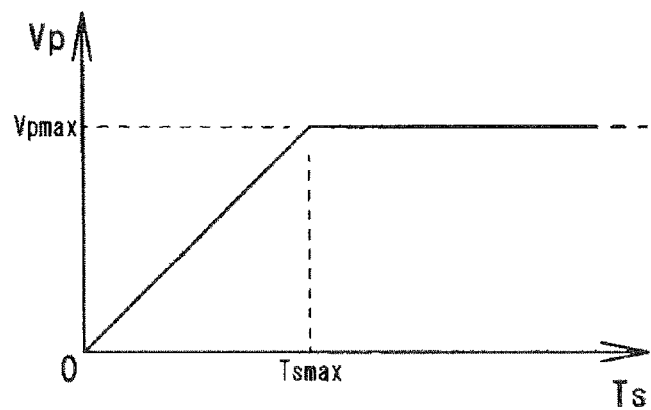
FIG. 7 illustrates a relationship between the preliminary liquid feeding volume Vp and the elapsed time Ts in the modified example of the first embodiment.

The preliminary liquid feeding volume Vp is a value required for releasing the air in the supply conduit 3 and filling the entirety of the inside of the supply conduit 3 with the liquid F in the preliminary liquid feeding process to be executed next. The longer the elapsed time Ts, the larger the preliminary liquid feeding volume Vp becomes. The preliminary liquid feeding volume Vp is determined based on a reference table as shown in FIG. 7, for example.

Note that, similarly as in the above-described embodiment, if the elapsed time Ts is longer than the predetermined time Tsmax, the preliminary liquid feeding volume Vp is set to a constant maximum value Vpmax irrespective of the length of the elapsed time Ts.

In the preliminary liquid feeding process, as shown in step S15a, the volume of the fed liquid F is calculated based on the detection result by the liquid flow detection section 5 as the flowmeter, and after the confirmation that the volume has reached the preliminary liquid feeding volume Vp as the target value, the processing proceeds to step S16, to stop the liquid feeding section 4.

Since the operating time of the liquid feeding section 4 and the volume of the liquid F are in the proportional relationship, there is no difference between the effect in the present modified example and that in the above-described embodiment. However, in the preliminary liquid feeding process in the modified example, the volume of the actually fed liquid F is recognized, which enables the air venting to be more surely performed.

Second Embodiment

Next, description will be made on the second embodiment of the present invention. Hereinafter, only the points different from the first embodiment will be described. The same constituent elements as those in the first embodiment are attached with the same reference numerals and description thereof will be appropriately omitted.

Figure 8:
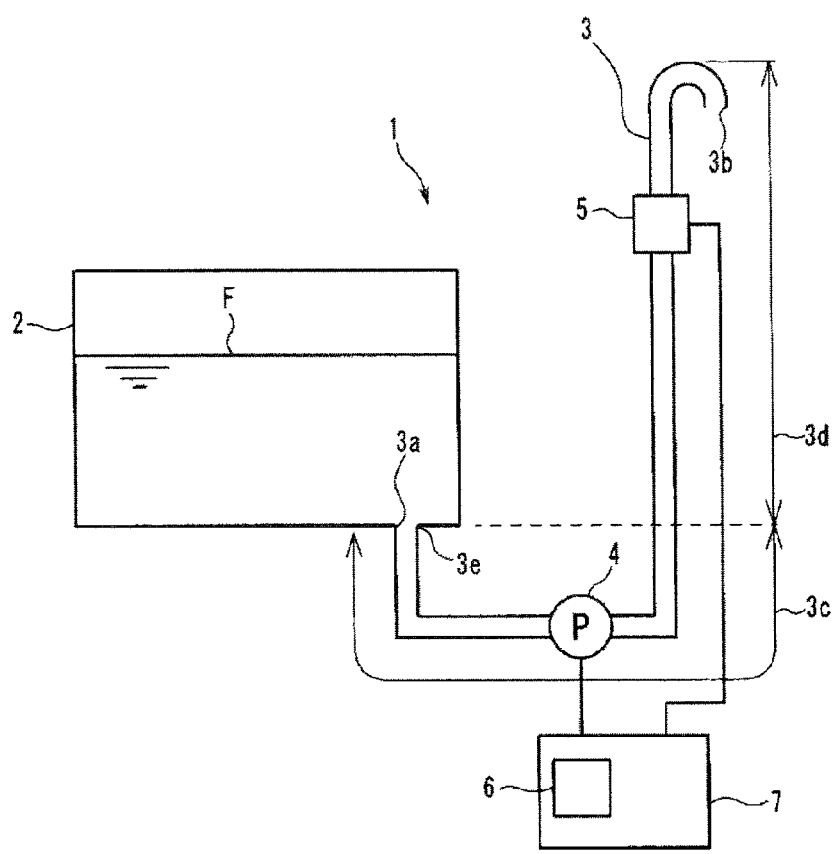
FIG. 8 illustrates a configuration of a liquid supply apparatus according to a second embodiment.

In the above-described first embodiment, the liquid flow detection section 5 is arranged at the first conduit 3c. In the present embodiment, the liquid flow detection section 5 is arranged at the second conduit 3d, as shown in FIG. 8.

Figure 9:
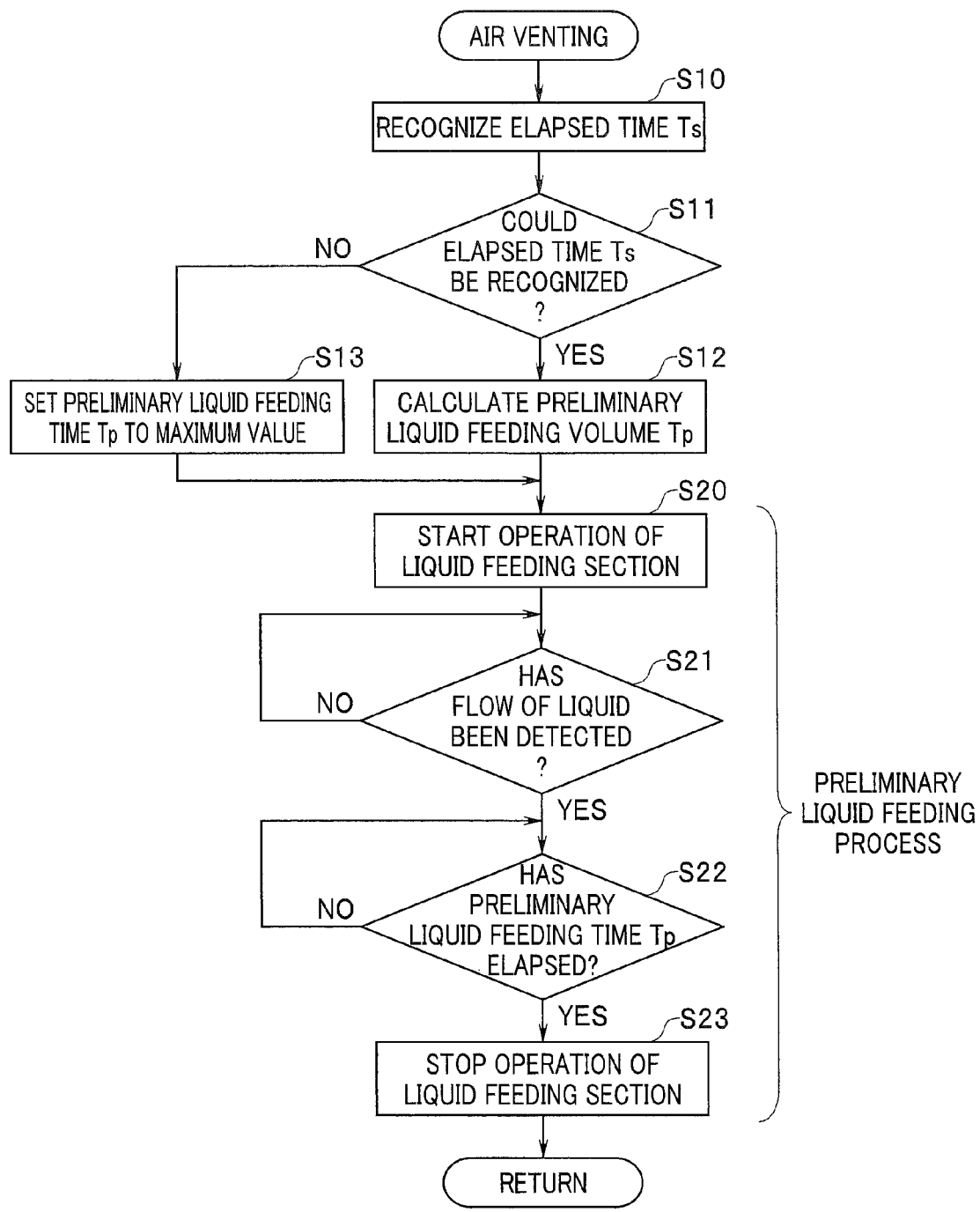
FIG. 9 is a flowchart of an air venting process according to the second embodiment.

When the liquid flow detection section 5 is arranged at the second conduit 3d as in the present embodiment, there is a case where the liquid level of the liquid F in the supply conduit 3 falls below the liquid flow detection section 5 depending on the elapsed time Ts after the stop of the liquid feeding in the main liquid feeding process. Therefore, in the preliminary liquid feeding process in the liquid supply apparatus 1 according to the present embodiment, as shown in the flowchart in FIG. 9, after the operation of the liquid feeding section 4 is started in step S20, a waiting state continues until the liquid feeding section 4 detects the flow of the liquid F as shown in step S21.

At the start of the step S21, if the liquid level is located above the liquid flow detection section 5, the flow of the liquid F is instantly detected and the processing proceeds to step S22. On the other hand, at the start of the step S21, if the liquid level is located below the liquid flow detection section 5, after the liquid level rises to the height of the liquid flow detection section 5 and the flow of the liquid F is detected by the liquid flow detection section 5, the processing proceeds to the step S22. In the step S22, the operation of the liquid feeding section 4 is continued only for the predetermined preliminary liquid feeding time Tp.

That is, at the start of the step S22, the liquid level in the supply conduit 3 is always located above the liquid flow detection section 5. The preliminary liquid feeding time Tp in the present embodiment is the operating time of the liquid feeding section 4, which is required for releasing the air present in the section of the supply conduit 3, that is, the section from the second end portion 3b to the part where the liquid flow detection section 5 is arranged. In the present embodiment, the elapsed time Ts at which the preliminary liquid feeding time Tp becomes the maximum value Tpmax is the time required for the liquid level of the liquid F remained in the supply conduit 3 to fall from the height of the second end portion 3b to the height at which the liquid flow detection section 5 is arranged.

Note that, also in the present embodiment, similarly as in the modified example of the first embodiment, the liquid feeding in the air venting process may be performed based on the volume of the liquid F detected by the liquid flow detection section 5.

Similarly as in the first embodiment, also in the present embodiment, the shorter the elapsed time Ts during which the liquid feeding section 4 is in the stopped state, the shorter the preliminary liquid feeding time Tp is set. As a result, the consumption amount of the liquid F in the air venting process can be reduced, and the time required for the air venting process can be reduced.

Third Embodiment

Next, the third embodiment of the present invention will be described. Hereinafter, only the points different from the first and second embodiments will be described below. The same constituent elements as those in the first and second embodiments are attached with the same reference numerals and descriptions thereof will be appropriately omitted.

Figure 10:
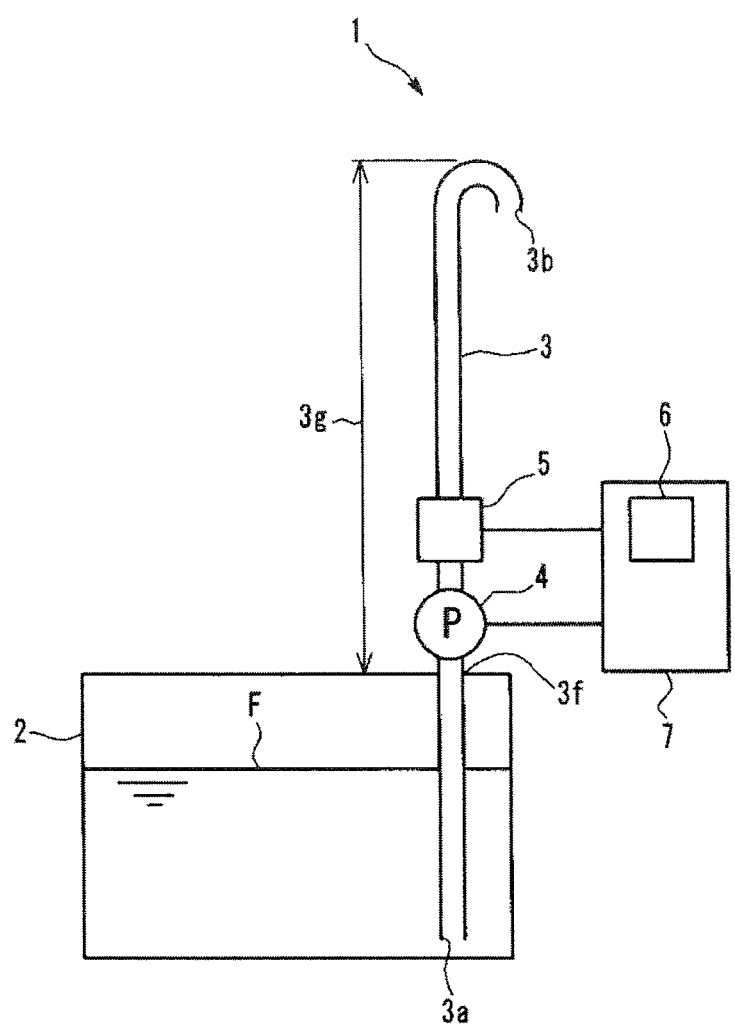
FIG. 10 illustrates a configuration of a liquid supply apparatus according to a third embodiment.

In the liquid supply apparatus 1 in the above-described first embodiment, the supply conduit 3 includes the first conduit 3c which is the section disposed at the position lower than the storing tank 2. On the other hand, in the liquid supply apparatus 1 according to the present embodiment shown in FIG. 10, the supply conduit 3 is arranged so as not to pass below the storing tank 2.

Specifically, the supply conduit 3 according to the present embodiment is arranged such that the entirety of the supply conduit 3 is located at the position upper than the bottom face of the storing tank 2. The first end portion 3a of the supply conduit 3 opens in the storing tank 2, and the second end portion 3b opens outside the storing tank 2. The second end portion 3b of the supply conduit 3 is disposed at the position upper than the maximum liquid level height of the storing tank 2.

More specifically, the supply conduit 3 is connected to the storing tank 2 at a third connection portion 3f, and includes a third conduit 3g located at a position upper than the third connection portion 3f. The third connection portion 3f is provided on the upper face of the storing tank 2, and the section of the supply conduit 3, which is located at the position upper than the storing tank 2, is the third conduit 3g.

The liquid feeding section 4 is arranged at the third conduit 3g at the position apart by a predetermined distance from the third connection portion 3f toward the second end portion 3b. The liquid feeding section 4 serves, while being in the stopped state, as the constriction section that constricts the cross-sectional area of the third conduit 3g. Note that the liquid feeding section 4 may be provided with a loose check valve that does not completely block the flow of the fluid in the supply conduit 3 from the second end portion 3b toward the first end portion 3a.

The liquid flow detection section 5 is arranged at a position upper than the liquid feeding section 4, that is, arranged at the third conduit 3g so as to be located on the second end portion 3b side with respect to the liquid feeding section 4.

In the present embodiment, similarly as in the second embodiment, there is a case where the liquid level of the liquid F in the liquid feeding conduit 3 falls below the liquid flow detection section 5 depending on the length of the elapsed time Ts. Therefore, in the preliminary liquid feeding process by the liquid supply apparatus 1 according to the present embodiment, as shown in the flowchart in FIG. 9 which is similar to the second embodiment, after the operation of the liquid feeding section 4 is started in the step S20, a waiting state continues until the flow of the liquid F is detected by the liquid feeding section 4 as shown in the step S21.

At the start of the step S21, if the liquid level is located above the liquid flow detection section 5, the flow of the liquid F is instantly detected, and the processing proceeds to step S22. On the other hand, at the start of the step S21, if the liquid level is located below the liquid flow detection section 5, after the liquid level rises to the height of the liquid flow detection section 5 and the flow of the liquid F is detected by the liquid flow detection section 5, the processing proceeds to the step S22. In the step S22, the operation of the liquid feeding section 4 is continued only for the predetermined preliminary liquid feeding time Tp.

That is, at the start of the step S22, the liquid level in the supply conduit 3 is always located above the liquid flow detection section 5. The preliminary liquid feeding time Tp in the present embodiment is the operation time of the liquid feeding section 4, which is required for releasing the air present in the section of the supply conduit 3, that is, the section from the second end portion 3b to the position where the liquid flow detection section 5 is arranged. Furthermore, in the present embodiment, the elapsed time Ts at which the preliminary liquid feeding time Tp becomes the maximum value Tpmax is the time required for the liquid level of the liquid F remained in the supply conduit 3 to fall from the height of the second end portion 3b to the height at which the liquid flow detection section 5 is arranged.

Note that, also in the present embodiment, similarly as in the modified example of the first embodiment, the liquid feeding in the air venting process may be performed based on the volume of the liquid F detected by the liquid flow detection section 5.

Also in the present embodiment, similarly as in the first and second embodiments, the shorter the elapsed time Ts during which the liquid feeding section 4 is in the stopped state, the shorter the preliminary liquid feeding time Tp is set. As a result, the consumption amount of the liquid F in the air venting process can be reduced, and the time required for the air venting process can be reduced.

Fourth Embodiment

Next, description will be made on the fourth embodiment of the present invention. Hereinafter, only the points different from the first to third embodiments will be described below. The same constituent elements as those in the first to third embodiments are attached with the same reference numerals and descriptions thereof will be appropriately omitted.

In the above-described first to third embodiments, the liquid supply apparatus 1 is provided in the endoscope reprocessing apparatus 20. However, the liquid supply apparatus 1 can be applied to another apparatus that uses the liquid F.

Figure 11:
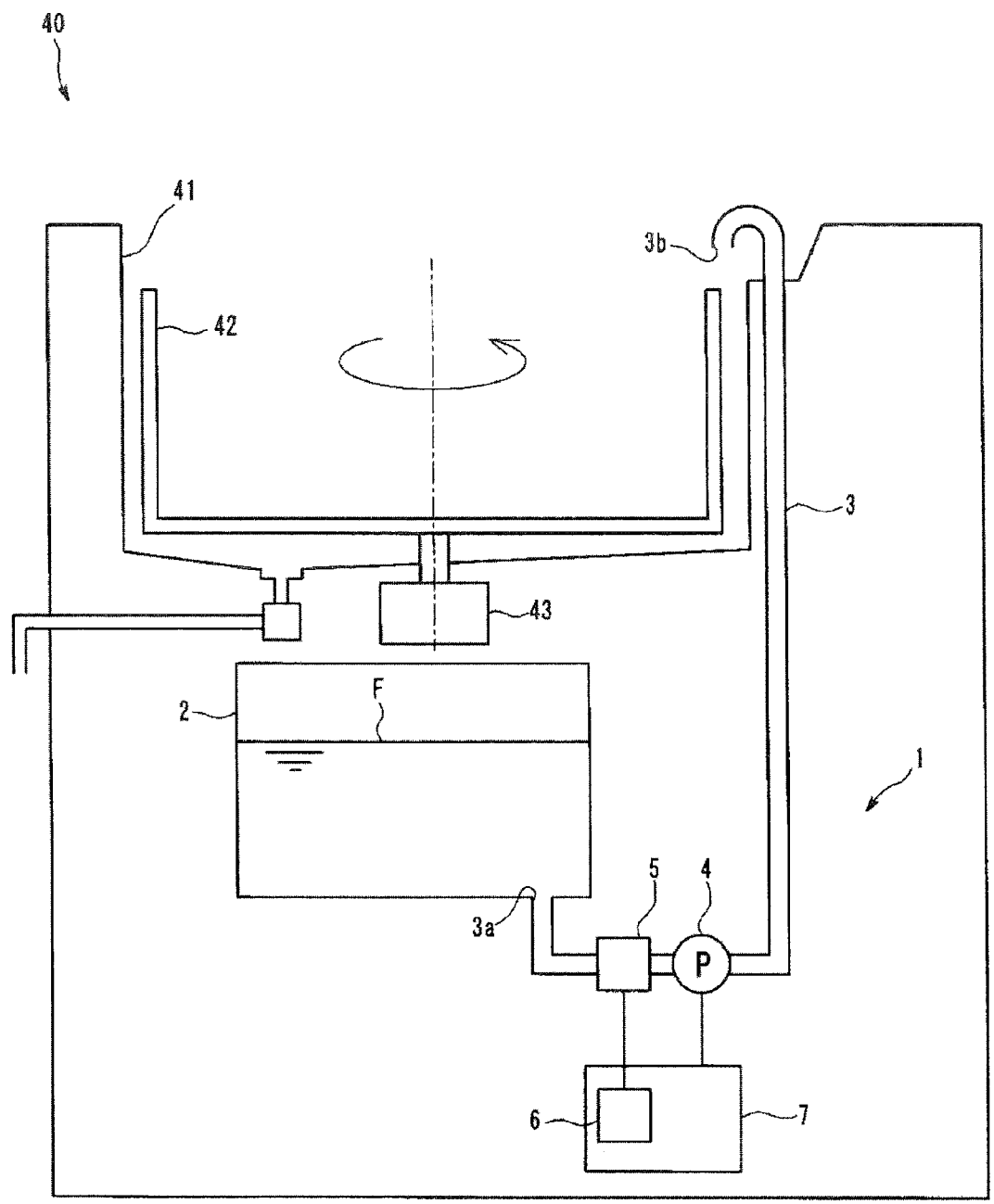
FIG. 11 illustrates a configuration of a washing machine provided with a liquid supply apparatus according to a fourth embodiment.

As one example in the present embodiment, the liquid supply apparatus 1 is provided in a washing machine 40, as shown in FIG. 11. The washing machine 40 is an apparatus for cleaning clothes and the like placed in the processing basin 41 by using the liquid F as the cleaning solution and water. The washing machine 40 is provided with a drum 42 that rotates in the processing basin 41. The drum 42 is driven to be rotated with an electric motor 43 and stirs the liquid in the processing basin 41.

The liquid supply apparatus 1 pours the liquid F as the cleaning solution into the processing basin 41 by a predetermined amount at a predetermined time. The configuration and motion of the liquid supply apparatus 1 are the same as those in the first embodiment. Therefore, the liquid supply apparatus 1 according to the present embodiment is capable of reducing the consumption amount of the liquid F in the air venting process, and also reducing the time required for the air venting process.

Note that the washing machine 40 shown in FIG. 11 is provided with the liquid supply apparatus 1 same as the one in the first embodiment. However, the washing machine 40 may be provided with the liquid supply apparatus 1 same as the one in the second or third embodiment.

Fifth Embodiment

Next, description will be made on the fifth embodiment of the present invention. Hereinafter, only the points different from the first to third embodiments will be described below. The same constituent elements as those in the first to third embodiments are attached with the same reference numerals and descriptions thereof will be appropriately omitted.

Figure 12:
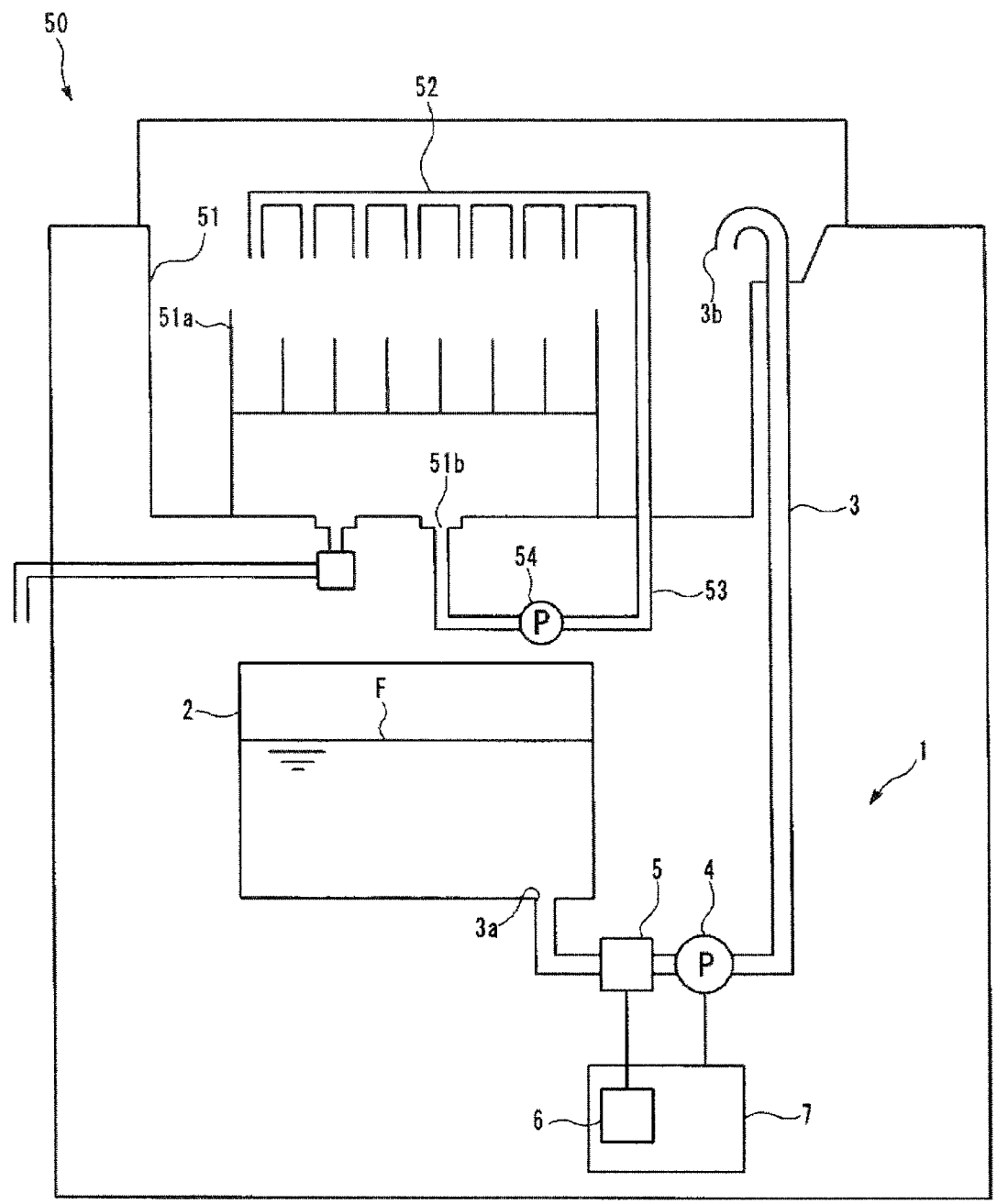
FIG. 12 illustrates a configuration of a dishwasher provided with a liquid supply apparatus according to a fifth embodiment.

In the present embodiment, the liquid supply apparatus 1 is provided in a dish washer 50 as one example, as shown in FIG. 12.

The dish washer 50 is an apparatus for washing dishes, etc., placed in a processing basin 51 by using the liquid F as the cleaning solution and water.

The dish washer 50 includes, inside the processing basin 51, a holding shelf 51a that holds the dishes. In addition, inside the processing basin 51, a nozzle 52 that spouts the liquid to the dishes placed on the holding shelf 51a is provided.

The processing basin 51 includes, at the bottom thereof, a circulation port 51b connected with the nozzle 52 through a circulation conduit 53. The circulation conduit 53 is provided with a circulation pump 54. Operating the circulation pump 54 allows the liquid in the processing basin 51 to be sucked from the circulation port 51b and thereafter to be passed through the circulation conduit 53 and spouted from the nozzle 52.

The liquid supply apparatus 1 pours the liquid F as the cleaning solution into the processing basin 51 by a predetermined amount at a predetermined time. The configuration and motion of the liquid supply apparatus 1 are the same as those in the first embodiment. Therefore, the liquid supply apparatus 1 according to the present embodiment is capable of reducing the consumption amount of the liquid F in the air venting process, and also reducing the time required for the air venting process.

Note that the dish washer 50 shown in FIG. 12 is provided with the liquid supply apparatus 1 same as the one in the first embodiment. However, the dish washer 50 may be provided with the liquid supply apparatus 1 same as the one in the second or third embodiment.

Note that the present invention is not limited to the above-described embodiments, and can be properly changed within the range without departing from the gist or the idea of the invention that can be read from claims and the entire description, and a liquid supply apparatus and an endoscope reprocessing apparatus accompanied by such changes are also included in the technical range of the present invention.

What is claimed is:

1. A liquid supply apparatus comprising:
    a storing tank configured to store a liquid;
    a supply conduit through which the liquid remained inside the supply conduit flows reversely into the storing tank by a predetermined amount over time, the supply conduit having a first end portion connected to the storing tank;
    a liquid feeding section which is arranged at the storing tank or the supply conduit, and which is configured to feed the liquid from the storing tank to a second end portion of the supply conduit;
    a time measuring section which measures an elapsed time from stop of the liquid feeding by the liquid feeding section; and
    a control section which is connected to the liquid feeding section and the time measuring section and which is configured to drive the liquid feeding section for a predetermined time based on a length of the elapsed time.

2. The liquid supply apparatus according to claim 1, further comprising,
    a liquid flow detection section which is configured to detect a flow of the liquid in the supply conduit,
    wherein the time measuring section measures an elapsed time from a clock time at which the stop of the liquid feeding by the liquid feeding section is detected by the liquid flow detection section.

3. The liquid supply apparatus according to claim 1, wherein the supply conduit includes a first connection portion connected to the storing tank, and further includes a first conduit arranged at a position lower than the storing tank in a direction of gravitational force, and a second conduit which connects the first conduit and the second end portion and which is arranged at a position upper than the first connection portion in the direction of gravitational force.

4. The liquid supply apparatus according to claim 1, wherein
the supply conduit includes a third connection portion which is arranged at a position upper than the storing tank in a direction of gravitational force and which is connected to the storing tank, and a third conduit arranged at a position upper than the third connection portion in the direction of gravitational force, and
the supply conduit includes, at a position apart by a predetermined distance from the third connection portion, a constriction section that constricts the third conduit.

5. The liquid supply apparatus according to claim 4, wherein the constriction section is a check valve that causes the liquid of a predetermined flow rate to flow reversely.

6. The liquid supply apparatus according to claim 4, wherein the liquid feeding section is a pump including therein the constriction section.

7. An endoscope reprocessing apparatus comprising:
the liquid supply apparatus according to claim 1; and
a processing basin in which an endoscope can be arranged and into which the liquid supplied from the liquid supply apparatus is introduced.

\* \* \* \* \*